US009357339B2

(12) United States Patent
Son et al.

(10) Patent No.: US 9,357,339 B2
(45) Date of Patent: *May 31, 2016

(54) PROXY COMMUNICATION SYSTEM AND CONTROL METHOD THEREOF IN BAN ENVIRONMENT

(71) Applicant: Samsung Electronics Co. Ltd., Suwon-si, Gyeonggi-do (KR)

(72) Inventors: Jae-Seung Son, Suwon-si (KR); Sun-Gi Gu, Yongin-si (KR); Seung-Hoon Park, Seoul (KR); Tae-Han Bae, Seoul (KR); Eun-Tae Won, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 16 days.

This patent is subject to a terminal disclaimer.

(21) Appl. No.: 14/356,768

(22) PCT Filed: Nov. 8, 2012

(86) PCT No.: PCT/KR2012/009407
§ 371 (c)(1),
(2) Date: May 7, 2014

(87) PCT Pub. No.: WO2013/069989
PCT Pub. Date: May 16, 2013

(65) Prior Publication Data
US 2014/0315494 A1 Oct. 23, 2014

(30) Foreign Application Priority Data
Nov. 8, 2011 (KR) .................. 10-2011-0116032

(51) Int. Cl.
H04B 7/00 (2006.01)
H04W 4/00 (2009.01)
(Continued)

(52) U.S. Cl.
CPC ............. *H04W 4/008* (2013.01); *A61B 5/0002* (2013.01); *G08C 17/02* (2013.01); *H04L 67/28* (2013.01);
(Continued)

(58) Field of Classification Search
CPC ... H04W 4/005; H04W 4/008; H04W 76/023; H04B 13/005
USPC .................................... 455/41.1, 41.2, 426.1
See application file for complete search history.

(56) References Cited

U.S. PATENT DOCUMENTS 7,113,994 B1 9/2006 Swift et al.
8,274,360 B2 * 9/2012 Sampath ................ G06Q 50/22
340/12.25

(Continued)

FOREIGN PATENT DOCUMENTS

EP 2 730 037 A2 5/2014
KR 20060103152 A 9/2006
KR 20110090422 A 8/2011

OTHER PUBLICATIONS

K. Kwak et al., "A study on proposed IEEE 802.15 WBAN MAC protocols.", 2009 ISCIT, pp. 834-840, Sep. 28-30, 2009. Figs. 3,4 on pp. 834-840, Section 2.

Primary Examiner — Marceau Milord
(74) Attorney, Agent, or Firm — Jefferson IP Law, LLP

(57) ABSTRACT

Disclosed is a control method of a communication system including at least one sensor that a user wears, a wireless communication apparatus and a coordinator. The control method of the communication system includes: in the coordinator, receiving a proxy authority request for proxy with respect to the at least one sensor and the coordinator from the wireless communication apparatus, and granting the proxy authority to the wireless communication apparatus; in the wireless communication apparatus, creating a user identifier corresponding to the user; in the wireless communication apparatus, searching for the at least one sensor that the user wears, and forming a pairing with the at least one found sensor; in the wireless communication apparatus, making a request to the at least one found sensor for association information for the association with the coordinator and the sensor, and receiving the association information; in the wireless communication apparatus, making a request to the coordinator for association proxy for an association between the at least one found sensor and the coordinator, and receiving the association proxy in response to the request; and in the coordinator, requesting data by forming an association with the at least one found sensor, and receiving data corresponding to the data request.

33 Claims, 18 Drawing Sheets

(51) Int. Cl.
*A61B 5/00* (2006.01)
*G08C 17/02* (2006.01)
*H04L 29/08* (2006.01)
*H04W 12/06* (2009.01)

(52) U.S. Cl.
CPC ......... *H04W 4/005* (2013.01); *G08C 2201/112* (2013.01); *G08C 2201/114* (2013.01); *H04W 12/06* (2013.01)

(56) References Cited

U.S. PATENT DOCUMENTS

| | | | | |
|---|---|---|---|---|
| 8,310,336 B2* | 11/2012 | Muhsin | ............. | G06F 17/30516 340/12.25 |
| 8,380,977 B2* | 2/2013 | Son | .................... | H04L 63/0428 380/270 |
| 8,405,502 B2* | 3/2013 | Teague | ................. | A61B 5/0024 340/286.02 |
| 9,000,914 B2* | 4/2015 | Baker | ................... | A61B 5/0002 340/5.22 |
| 2006/0217072 A1 | 9/2006 | Poyhonen et al. | | |
| 2010/0045425 A1 | 2/2010 | Chivallier | | |
| 2011/0025493 A1* | 2/2011 | Papadopoulos | .... | A61B 5/02427 340/539.12 |
| 2011/0221590 A1 | 9/2011 | Baker et al. | | |
| 2012/0083705 A1* | 4/2012 | Yuen | .................... | A61B 5/0002 600/508 |
| 2012/0202425 A1* | 8/2012 | Glezerman | ........... | H04W 84/18 455/41.2 |
| 2013/0201316 A1* | 8/2013 | Binder | .................... | H04L 67/12 348/77 |
| 2014/0106673 A1* | 4/2014 | Son | ..................... | A61B 5/0024 455/41.1 |

\* cited by examiner

| Device ID | Capability Information | Reserved Field |

| Alternate PAN Coordinator | Device Type | Power Source | Receiver On When Idle | Reserved | Security Capability | Allocate Address |
|---|---|---|---|---|---|---|
| Octets: 2 | 1 | 2 | 3 | 4-5 | 6 | 7 |

FIG.3G

| MAC Header | Command Frame Identifier | Association Information |

| User ID | Device ID List | Capability Information List | Reserved Field |

FIG.3H

| MAC Header | Command Frame Identifier | Command Payload |

| Association Status | Reserved Field |

FIG.3I

PROXY COMMUNICATION SYSTEM AND CONTROL METHOD THEREOF IN BAN ENVIRONMENT

CROSS-REFERENCE TO RELATED APPLICATION(S)

This application is a U.S. National Stage application under 35 U.S.C. §371 of an International application filed on Nov. 8, 2012 and assigned application number PCT/KR2012/009407, and claims the benefit of a Korean patent application filed on Nov. 8, 2011 in the Korean Intellectual Property Office and assigned Serial number 10-2011-0116032, the entire disclosure of which is hereby incorporated by reference.

TECHNICAL FIELD

The present invention relates to a proxy communication system and a control method thereof in the BAN environment, and more particularly, to a proxy communication system and a control method thereof in the BAN environment by which medical or entertainment services can be operated.

BACKGROUND ART

Recently, vibrant studies of a communication system associated with the medical related field are in progress. A communication system for the medical related field is generally comprised of a sensor that patients wear for detecting bio-signals output from the patients, and a coordinator that is connected with the sensor to collect data.

The patient wears at least one sensor on his/her body, and each of the at least one sensor detects different bio-signals output from the patient to thereby process data. Meanwhile, the coordinator may receive data output from the at least one sensor, and process a plurality of data in totality to analyze overall health conditions of the patient.

However, the sensor and the coordinator are connected by a wire in most communication systems for the medical related field. Accordingly, a coordinator should be provided to every single patient which causes a high cost.

Furthermore, since the sensor attached to the patient's body is connected with the coordinator by a wire, the patient encounters behavioral restrictions. As the number of the sensors attached to the patient increases, the number of wired cables required for transmission and reception of data increases too. Accordingly, the patient is inconvenienced as their movement is restricted.

Meanwhile, recently, a discussion about standards for operating of medical or entertainment services such as IEEE 802.15.4 Zigbee or IEEE 802.15.6 Body Area Network (hereinafter referred to as BAN) is in progress, and the development of a wireless communication system between the sensor and the coordinator using these standards is required.

DETAILED DESCRIPTION OF THE INVENTION

Technical Problem

The present invention has been made in order to solve the above-mentioned problems and meet the above-mentioned requirement, and the present invention provides a communication system including proxy devices by which transmission and reception of signals between a coordinator and a sensor can be performed by a wireless connection in the BAN environment.

Technical Solution

In order to address the above problems, a first aspect of the present invention provides a control method of a communication system including at least one sensor that a user wears, a wireless communication apparatus and a coordinator, the method including: in the coordinator, receiving a proxy authority request for proxy with respect to the at least one sensor and the coordinator from the wireless communication apparatus, and granting the proxy authority to the wireless communication apparatus; in the wireless communication apparatus, creating a user identifier corresponding to the user; in the wireless communication apparatus, searching for the at least one sensor that the user wears, and forming a pairing with the at least one found sensor; in the wireless communication apparatus, requesting association information from the at least one found sensor for the association with the coordinator and the sensor, and receiving the association information; in the wireless communication apparatus, requesting the association proxy from the coordinator for the association between the at least one found sensor and the coordinator, and receiving the association proxy in response to the request; and in the coordinator, requesting data by forming an association with the at least one found sensor, and receiving data corresponding to the data request.

In a communication system including at least one sensor that a user wears, a wireless communication apparatus and a coordinator in accordance with a second aspect of the present invention, the coordinator includes: a first communication unit that receives a proxy authority request data for proxy with respect to the at least one sensor and the coordinator from the wireless communication apparatus; and a first controller that controls the first communication unit to transmit the proxy authority in response to the proxy authority request.

Meanwhile, the wireless communication apparatus includes: a second communication unit that receives the proxy authority; and a second controller that creates a user identifier corresponding to the user and controls the second communication unit to search for the at least one sensor that the user wears to form a pairing with the at least one found sensor.

In addition, the at least one sensor includes: a third communication unit that receives an association information request for the association with the coordinator and the sensor from the wireless communication apparatus; and a third controller that controls the third communication unit to transmit the association information to the wireless communication apparatus in response to the request.

Here, the second controller controls the second communication unit to request the coordinator for the association proxy for the association between the at least one found sensor and the coordinator, and the second communication unit receives the association proxy corresponding to the request.

Further, the first controller controls the first communication unit to form association with the at least one found sensor and request data, and the third controller controls the third communication unit to transmit the data corresponding to the data request.

Advantageous Effects

In accordance with various embodiments of the present invention, transmission and reception of data between the coordinator and the sensor can be performed by a wireless connection, which creates a more convenient environment for the patient.

In addition, the coordinator authorizes the wireless communication apparatus, which serves as a medium to enable transmission and reception of data between the coordinator and the sensor, to act as a proxy for some or all of functions. The wireless communication apparatus authorized by the coordinator as set forth above operates as a proxy.

Accordingly, administrators like nurses who check the health of the patient possess proxy devices and approach the patient, so that bio-signal data of all the patients can be easily transmitted to the coordinator.

Furthermore, without providing a coordinator to every single patient, the single central coordinator receives the bio-signal data from each of the patients through the proxy device, so the cost required for providing several coordinators can be saved.

BRIEF DESCRIPTION OF THE DRAWINGS

FIGS. 3b to 3i illustrate frame formats according to various embodiments of the present invention;

FIGS. 6b and 6c illustrate frame formats of packets transmitted and received in the communication system of FIG. 6a.

MODE FOR CARRYING OUT THE INVENTION

Figure 1:
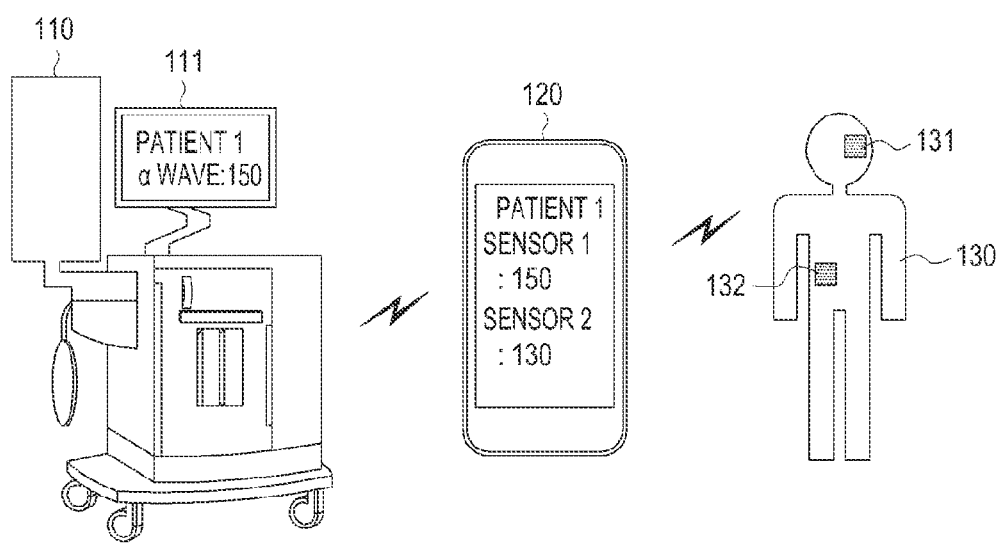
FIG. 1 is a conceptual diagram illustrating a communication system in the BAN environment according to an embodiment of the present invention.

Hereinafter, various embodiments of the present disclosure will be described more specifically with reference to the accompanying drawings. It should be noted that the same components of the drawings are designated by the same reference numeral anywhere. In the following description of the present invention, a detailed description of known functions and configurations incorporated herein will be omitted when it may make the subject matter of the present invention rather unclear.

FIG. 1 is a conceptual diagram illustrating a communication system in the BAN environment according to an embodiment of the present invention.

As shown in FIG. 1, a communication system in the BAN environment may include a coordinator 110, a wireless communication apparatus 120, and at least one sensor 131 and 132.

The coordinator 110 may receive data related to a bio-signal or the like that is output from the at least one sensor 131 and 132, then process the data on the basis of preset algorithms, programs, or applications, and output the processed result through a display means 111 or the like. Alternatively, the coordinator 110 may store input data, and display stored data or output stored data to other devices according to the user's manipulation.

The coordinator 110 may communicate with the wireless communication apparatus 120 that is a proxy device by wireless as shown in the drawing. The coordinator 110 may perform the communication with the wireless communication apparatus 120 using various well-known communication technologies such as general cellular communication, wireless-fidelity (Wi-Fi) communication, blue-tooth communication, near-field communication (NFC), or the like.

Meanwhile, the coordinator 110 may directly perform the communication with the at least one sensor 131 and 132, and the coordinator 110 may perform the communication with the at least one sensor 131 and 132 using, preferably, near-field communication technologies such as NFC communication, BAN communication, or the like. The type of communication between the coordinator 110 and the wireless communication apparatus 120, or between the coordinator and the sensors 131 and 132 may be implemented in various ways by those skilled in the art.

The wireless communication apparatus 120, which may be a kind of proxy device, may act as a proxy for pairing between the sensors 131 and 132 and the coordinator 110.

More specifically, the wireless communication apparatus 120 may request the coordinator 110 for proxy authority for proxy with respect to the at least one sensor 131 and 132 and the coordinator 110, and may be granted with the proxy authority from the coordinator 110.

Afterwards, the wireless communication apparatus 120 may create a user identifier corresponding to a user 130 who wears the sensors 131 and 132, and store information on the created user identifier. The wireless communication apparatus 120 may search for at least one sensor 131 and 132 that the user wears on the basis of the granted proxy authority.

The wireless communication apparatus 120 may search for and find the sensors around the wireless communication apparatus 120 in a manner in which the wireless communication apparatus 120 may broadcast an inquiry packet based on, for example, NFC or the like, and receive a response packet that the sensors 131 and 132 transmit in response to the broadcasting. Here, the inquiry packet that the wireless communication apparatus 120 broadcasts may be defined on the basis of a communication technique that is set up between the wireless communication apparatus 120 and the sensors 131 and 132, and it would be easily understood by those skilled in the art that the inquiry packet may be made to various modifications according to the set type of communication technique.

The wireless communication apparatus 120 may form a pairing with each of the found sensors 131 and 132. Here, the types of communication technique between the wireless communication apparatus 120 and each of the sensors 131 and 132 may be same or different. When the types of communication technique between the wireless communication apparatus 120 and each of the sensors 131 and 132 are same, the wireless communication apparatus 120 may time-sequentially form a pairing with one sensor first, and afterwards, may form another pairing with other sensor. When the types of communication technique between the wireless communication apparatus 120 and each of the sensors 131 and 132 are different, the wireless communication apparatus 120 may independently form the pairings with each of the sensors 131 and 132 at the same time.

Meanwhile, the wireless communication apparatus 120 may form the pairings with all of the found sensors, or may form the pairings with some of the found sensors according to the user's selection.

The wireless communication apparatus 120 may form the pairings with the sensors 131 and 132 as set forth above. Also, once the pairings are formed, the wireless communication apparatus 120 may sequentially or simultaneously make a request to each of the sensors 131 and 132 for association information for the association with the coordinator 110 and each of the sensors 131 and 132, and may receive the association information corresponding to each of the sensors 131 and 132 from the sensors 131 and 132. Here, the association information may include information on each of the sensors 131 and 132 or information on the user identifier that is received from the wireless communication apparatus 120, and the association information will be described in detail later.

Afterwards, the wireless communication apparatus 120 may make a request to the coordinator 110 for an association proxy for the association between at least one found sensors 131 and 132 and the coordinator 110, and receive the association proxy corresponding to the request. Here, the association proxy may include an identifier of the wireless communication apparatus 120, a user identifier, information on each of the sensors 131 and 132, and the like, and the association proxy will be described in detail later.

The sensors 131 and 132 may be attached to the body of the user and receive bio-signals output from the body of the user. The sensors 131 and 132 may process the received bio-signals into a data form capable of being transmitted through the communication, and transmit and receive the processed data to and from the coordinator 110 or the wireless communication apparatus 120.

The sensors 131 and 132 may form the pairing with the wireless communication apparatus 120, and transmit the association information in response to the request from the wireless communication apparatus 120, as described above.

In addition, the sensors 131 and 132 may receive an association response indicating that the association between the sensors 131 and 132 and the coordinator 110 has been formed from the coordinator 110. Further, the sensors 131 and 132 may receive a request for data transmission from the coordinator 110, and transmit data corresponding to the received data transmission request to the coordinator 110.

As described above, the coordinator 110 may communicate with the wireless communication apparatus 120 or the sensors 131 and 132 by a wireless connection, and particularly, a proxy device such as the wireless communication apparatus 120 may be involved in the communication system to establish more efficient and stable data management.

Hereinafter, operations related to various embodiments of the communication system in the BAN environment will be described in more detail on the basis of timing diagrams.

Figure 2:
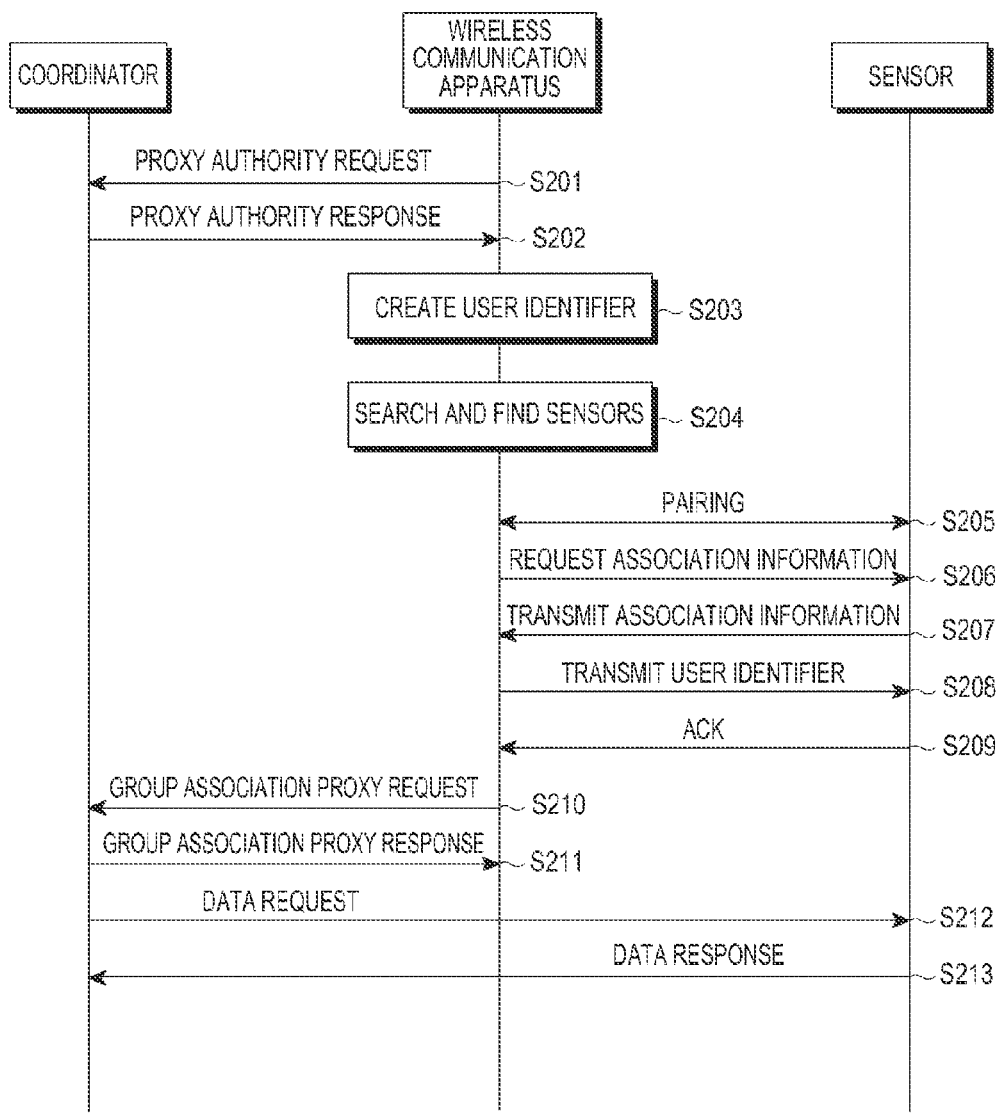
FIG. 2 is a timing diagram of a control method of a communication system according to an embodiment of the present invention.

FIG. 2 is a timing diagram of a control method of a communication system according to an embodiment of the present invention. The communication system of FIG. 2 includes a coordinator and a wireless communication apparatus, and it is assumed that the wireless communication apparatus searches for and finds a single sensor in the embodiment of FIG. 2.

As shown in FIG. 2, the wireless communication apparatus may a make request to the coordinator for proxy authority (S201). Here, the proxy authority may be a requesting authority by which the wireless communication apparatus may act as a proxy for some or all of functions of the coordinator. For example, the authorized wireless communication apparatus may have authority to act as a proxy for a connecting operation between the coordinator and the sensor, and in relation to this, a more detailed description related to data fields or the like will follow later.

The coordinator may grant the proxy authority to the wireless communication apparatus in response to the received proxy authority request (S202).

The wireless communication apparatus may preferentially create a user identifier corresponding to a user who wears the sensor on the basis of the received proxy authority (S203). The user identifier may be used to provide information on the user wearing each sensor later.

Here, the wireless communication apparatus may create the user identifier on the basis of an external input. Alternatively, the wireless communication apparatus may create the user identifier on the basis of an RF signal related to user information that is received from a RFID tag or a RF signal generator, which is located around the user. Meanwhile, apart from the wireless communication apparatus, the user identifier may be created in various ways, and it would be easily understood by those skilled in the art that there is no limitation in relation to the procedure of creation of the user identifier.

The wireless communication apparatus may search for and find sensors around the wireless communication apparatus (S204). The wireless communication apparatus may broadcast the inquiry packet in order to search for the sensors as set forth above, and check a received response packet or the like corresponding thereto to thereby find the sensors around the wireless communication apparatus. Preferably, the wireless communication apparatus may search for the sensors on the basis of a super near-field communication technique such as NFC.

The wireless communication apparatus may form a pairing with respect to the found sensor (S205). Here, the wireless communication apparatus may form pairings with respect to all of the found sensors, or some of the found sensors on the basis of the external input signal for selecting sensors.

The wireless communication apparatus may make a request to the sensor for association information for the association with the coordinator and the sensors (S206). Here, the association information may include information on a MAC header and the sensors, and data fields related thereto will be described in detail later.

Meanwhile, the sensors may include communication modules like a IEEE 802.15.4 Zigbee communication module. The sensors may keep the communication module disabled, and when the association information request signal is received, the sensors may convert the communication module to the enabled state. The communication module may wait until the data request is received from the coordinator.

The sensors may transmit the association information corresponding to the received association information request (S207).

When the wireless communication apparatus receives the association information from the sensor (S207), it may transmit the created user identifier to the sensor (S208). The sensor may store the received user identifier in a storage medium that is provided in the sensor. The sensor that has received the user identifier may transmit an acknowledge message to the wireless communication apparatus (S209).

Meanwhile, if the sensor is not provided with a special supplementary storage medium, the step of transmitting the user identifier by the wireless communication apparatus may be omitted. After the user identifier is stored, the sensor may transmit the user identifier when transmitting data to the coordinator so as to allow the coordinator to easily analyze which user wears the sensor.

The wireless communication apparatus may make a request to the coordinator for an association proxy for the association between the coordinator and the sensor (S210). Meanwhile, although the wireless communication apparatus is paired with a single sensor in FIG. 2, the wireless communication apparatus may be paired with two or more sensors, and in this case, a group association proxy may be requested (S210). Here, the association proxy may include the identifier of the wireless communication apparatus, the user identifier, information on the sensor, or the like, and data fields of the association proxy and a more detailed description will follow later.

The coordinator may transmit a response to the association proxy (S211) to the wireless communication apparatus. The coordinator may receive the association proxy request, and transmit the response thereto, so that the association between the coordinator and the sensor can be formed.

The coordinator may request predetermined data from the sensor (S212). Here, the data may be bio-signals collected from the body of the user or data processed in a preset manner, and the data and related data fields will be described in detail later.

The sensor may transmit data to the coordinator in response to the data request by the coordinator (S213). Alternatively, even though the coordinator does not request the transmission of data, the sensor may transmit information that is periodically monitored to the coordinator.

According to the above-described processes, the wireless communication apparatus may be implemented as a proxy device that acts as a proxy with respect to the found sensors. Accordingly, the data collected from the sensors that each user wears may be processed easily and effectively.

Figure 3A:
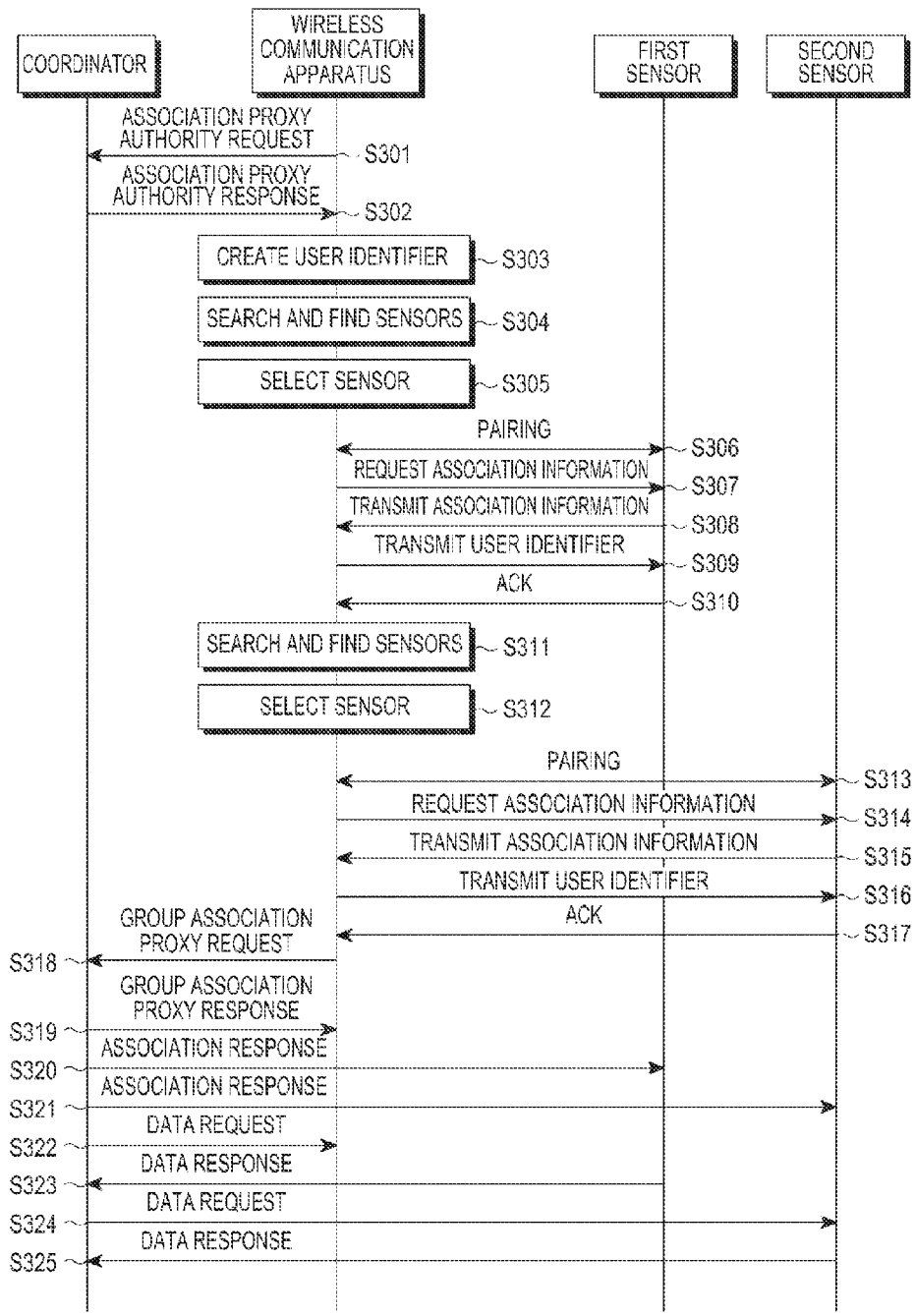
FIG. 3a is a timing diagram related to a control method of a communication system according to another embodiment of the present invention.

FIG. 3a is a timing diagram related to a control method of a communication system according to another embodiment of the present invention. Meanwhile, the description about the same configurations as those of the control method of the communication system related to FIG. 2 will be omitted or simplified.

The wireless communication apparatus may make a request to the coordinator for an association proxy authority (S301). The coordinator may grant the association proxy authority in response thereto (S302).

Figure 3B:
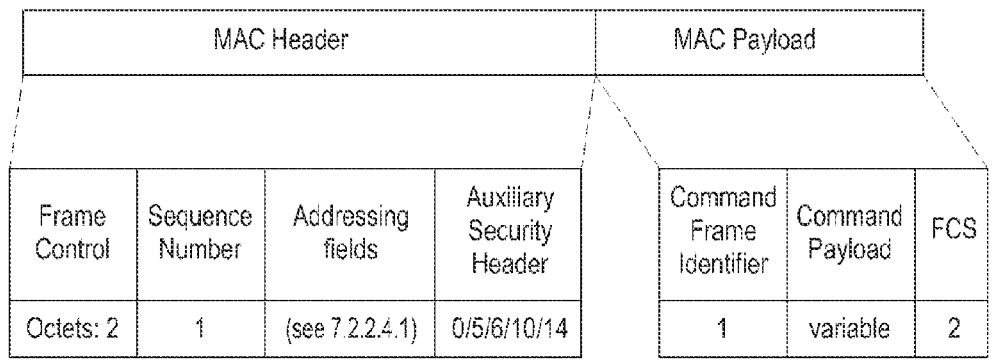

FIG. 3b shows a structure of an association proxy authority command frame. As shown in FIG. 3b, the association proxy authority command frame is comprised of a MAC header (hereinafter, referred to as MHR) and MAC payload. Here, the MHR is a header, and includes a frame control field, a sequence number field, an addressing field, and an auxiliary security header. The MAC payload includes a command frame identifier, command frame related information, and the like. The command frame identifier includes an association proxy authority request identifier or an association proxy authority response identifier.

The frame control field refers to the type of frame, use or non-use of security, a frame version, and the like. The sequence number denotes a sequence of frame transmission, and the addressing field refers to a Personal Area Network (PAN) ID and an address of the transmission/reception device. The auxiliary security field refers to how the frame is secured.

Meanwhile, in steps S301, S401, S501, S601 and S707 where the wireless communication apparatus requests the association proxy authority from the coordinator, the wireless communication apparatus may transmit the identifier of the wireless communication apparatus together with the association proxy authority request. The identifier of the wireless communication apparatus may be transmitted, while being included in a source address field (not shown) in the addressing field of the MHR field in FIG. 3b.

Meanwhile, the coordinator may store the wireless communication apparatus identifier received from the wireless communication apparatus, and grant the proxy authority to the wireless communication apparatus by transmission with the grant of the association proxy authority (S302, S403, S502, S602 and S702).

Figure 3C:
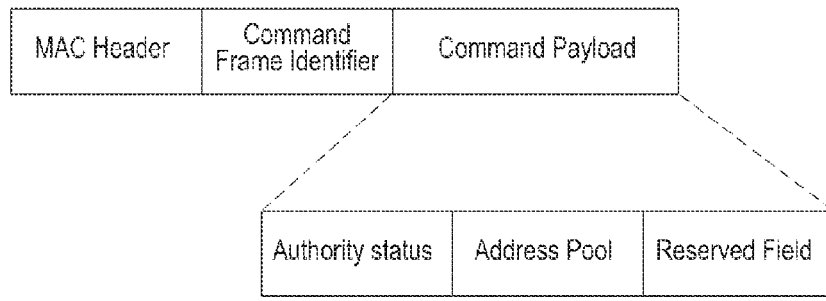

FIG. 3c shows a configuration of a message when an association proxy authority frame operates, including the association proxy authority response identifier according to an embodiment of the present invention. In this case, an authority status indicates the result of response to the proxy authority request, and an address pool is address information that the wireless communication apparatus transmits to the sensor. Reserved fields are allotted for later supplementary use.

Meanwhile, the association proxy authority request identifier may be transmitted using a frame format defined by IEEE 802.15.4. The frame format of IEEE 802.15.4 is comprised of an association request command field and an association proxy authority request field.

Figure 3D:
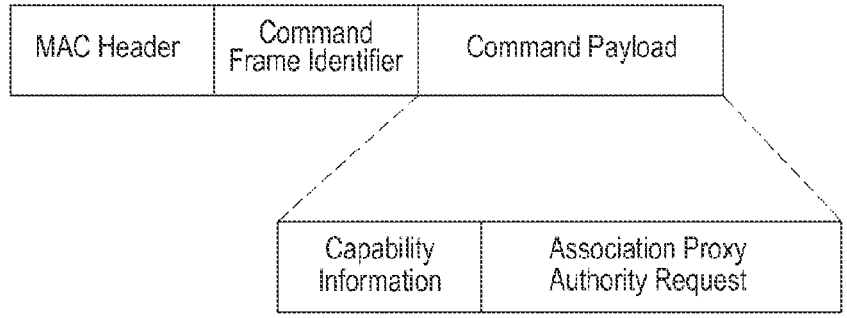

In detail, as shown in FIG. 3d, the association request command may include an MHR field, a command frame identifier, and capability information, and transmit the association proxy request identifier which is included in the association proxy authority request field.

After the wireless communication apparatus is granted the association proxy authority, it may create the user identifier (S303), and search for sensors around the wireless communication apparatus (S304). It is assumed that two sensors, i.e., a first sensor and a second sensor are found in the embodiment of FIG. 3a.

Meanwhile, the wireless communication apparatus may further find other sensors in addition to the first and the second sensors. If it is determined that the additionally found sensors are not attached to the corresponding user, the administrator may exclude the additionally found sensors from the pairing process by inputting the external signal to the interface or the like (S305). Meanwhile, based on the intensity of signals received from each of the sensors, when the intensity of the received signal is less than a preset value, the wireless communication apparatus may determine that the corresponding user is not wearing the sensor so that the sensor may be excluded from the pairing process. Besides, it would be easily understood by those skilled in the art that various modifications could be made.

The wireless communication apparatus may sequentially perform the pairing operation and the associating operation with respect to the two found sensors. For example, the wireless communication apparatus may first form the pairing with the first sensor, and afterwards form the pairing with the second sensor. Here, the pairing with the first sensor and the pairing with the second sensor may be performed on the basis of the same communication standard or on the basis of the different communication standards. Meanwhile, when the formation of the two pairings is based on different communication standards, the formation of the two pairings may be performed simultaneously and independently.

The wireless communication apparatus makes a request to the first sensor for association information for the associating operation (S306). The wireless communication apparatus may request the association information by transmitting an association information request frame to the first sensor. Meanwhile, the wireless communication apparatus may additionally transmit information on the coordinator, for example, information on the channel that the coordinator is using or the like, together with the request for the association information. The wireless communication apparatus may select and transmit one address from among the address pool received in the step S302 where the proxy authority is granted.

Figure 3E:
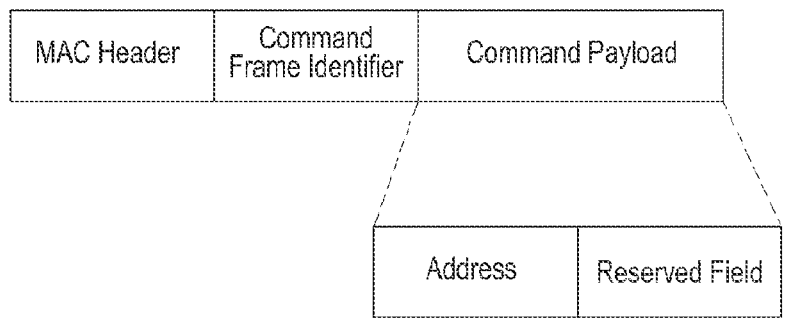

FIG. 3e is a conceptual diagram of a frame format of an association information request message (S307, S314, S407, S412, S506, S510, S606, S617, S707 and S717). As shown in FIG. 3e, the association information request message may include an MHR field, a command frame identifier, an address, and reserved fields.

Here, the MHR field is a MAC header, and it may be comprised of contents copied from the MHR field received from the coordinator. The command frame identifier refers to the type of the MAC command, and here, it is the identifier that indicates the association information request message. The address may be used by the sensor that performs communication with the coordinator. The reserved fields may be an allotted part to be used later.

The first sensor may transmit the association information to the wireless communication apparatus in response to the association information request (S308). After the association information is transmitted to the wireless communication apparatus, the first sensor may keep the communication module enabled, and wait until the association response is finally received from the coordinator. The first sensor may be set to wait for reception of the association response for a predetermined time, and the predetermined time may be set to be longer than the normal association waiting time, taking an administrator's behavior into account.

The first sensor may transmit the association information to the wireless communication apparatus by transmitting the association information response frame. Here, the association information response frame may include a device ID and sensor information.

Figure 3F:
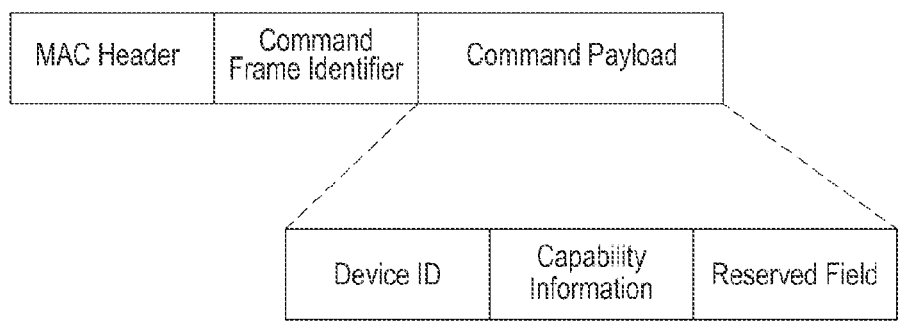

FIG. 3f shows a data frame format of an association information response message (S308, S408, S413, S507, S511, S607, S618, S708 and S718) according to an embodiment of the present invention. As shown in FIG. 3f, the association information response message may include an MHR field, a command frame identifier, a device ID, capability information, and reserved fields.

Here, the MHR field is a MAC header. The command frame identifier refers to the type of the MAC command, and here, it is an identifier that indicates the association information response message. The device ID may be an identifier of the first sensor that is transmitted to the coordinator.

In addition, the capability information may be information on the sensor, for example, information on the serial number, the type, the battery type, or the like. With regard to the capability information, if the information database on each sensor is constructed in the coordinator, the capability information may include only information such as the serial number or the like for identifying the sensor. Otherwise, if the information database on each sensor is not constructed in the coordinator, the capability information may include the above-described information including the serial number, the type, and the battery type. The reserved fields may be allotted for later use.

FIG. 3g illustrates a capability information field format of IEEE 802.15.4 as an example compared with the present invention. As shown in FIG. 3g, the capability information may refer to the device type, the power source, or the like.

Upon receiving the association information from the first sensor (S308), the wireless communication apparatus may transmit the created user identifier to the first sensor (S309). Here, it is assumed that the first sensor includes a storage means for storing the user identifier.

The first sensor transmits an acknowledgement frame to the wireless communication apparatus to notify whether the user identifier has been received or not (S310).

The wireless communication apparatus may repeat the pairing and associating operations with respect to the second sensor in the same manner as to the first sensor as described above (S311 to S317).

The wireless communication apparatus may make a request to the coordinator for the association proxy for the association between the first and second sensors and the coordinator (S318). Here, the wireless communication apparatus requests the association proxy of two sensors, which may be referred to as the group association proxy.

The wireless communication apparatus may transmit the group association proxy to the coordinator by transmitting the group association proxy request command frame to the coordinator. The group association proxy may include at least one of a wireless communication apparatus identifier, a user identifier, a device ID list, and a capability information list.

FIG. 3h shows a data frame format of a group association proxy request message (S318, S416, S512, S610, S621, S709 and S719) according to an embodiment of the present invention. As shown in FIG. 3h, the group association proxy request message may include an MHR field, a command frame identifier, and association information. Here, the MHR field is a MAC header, and the wireless communication apparatus identifier information is transmitted as the source address field.

The command frame identifier refers to the type of MAC command, and includes a group association request identifier, here. The association information is a portion of the payload of the MAC command, and it may include a user identifier, a device ID list, a capability information list, and reserved fields. The device ID list is the list of the paired sensors. In addition, the capability information list includes supplementary information (e.g., the device type, the power source, and the like) of each sensor.

The coordinator may transmit the group association proxy response in response to the group association proxy request from the wireless communication apparatus (S319). The coordinator may transmit the group association proxy response by transmitting the group association proxy response command frame.

FIG. 3i shows a frame format of a group association proxy response message (S319, S417, S513, S611, S622, S710 and S720) according to an embodiment of the present invention. As shown in FIG. 3i, the group association proxy response message may include an MHR field, a command frame identifier, an association status, and reserved fields.

Here, the MHR field is a MAC header. The command frame identifier refers to the type of the MAC command, and includes a group association response identifier in this embodiment. The association status indicates the result of the response to the association request, and the reserved fields may be allotted for later use.

The coordinator may transmit the association response to the first and the second sensors, respectively (S320 and S321). When the association response is received from the coordinator, it may be determined that the coordinator and the respective sensors have been associated. Accordingly, in response to the data request from the coordinator (S322 and S324), each sensor may transmit data corresponding to the data request (S323 and S325). Alternatively, although the coordinator does not request the data transmission, the sensors may periodically transmit information that is monitored to the coordinator.

Figure 4:
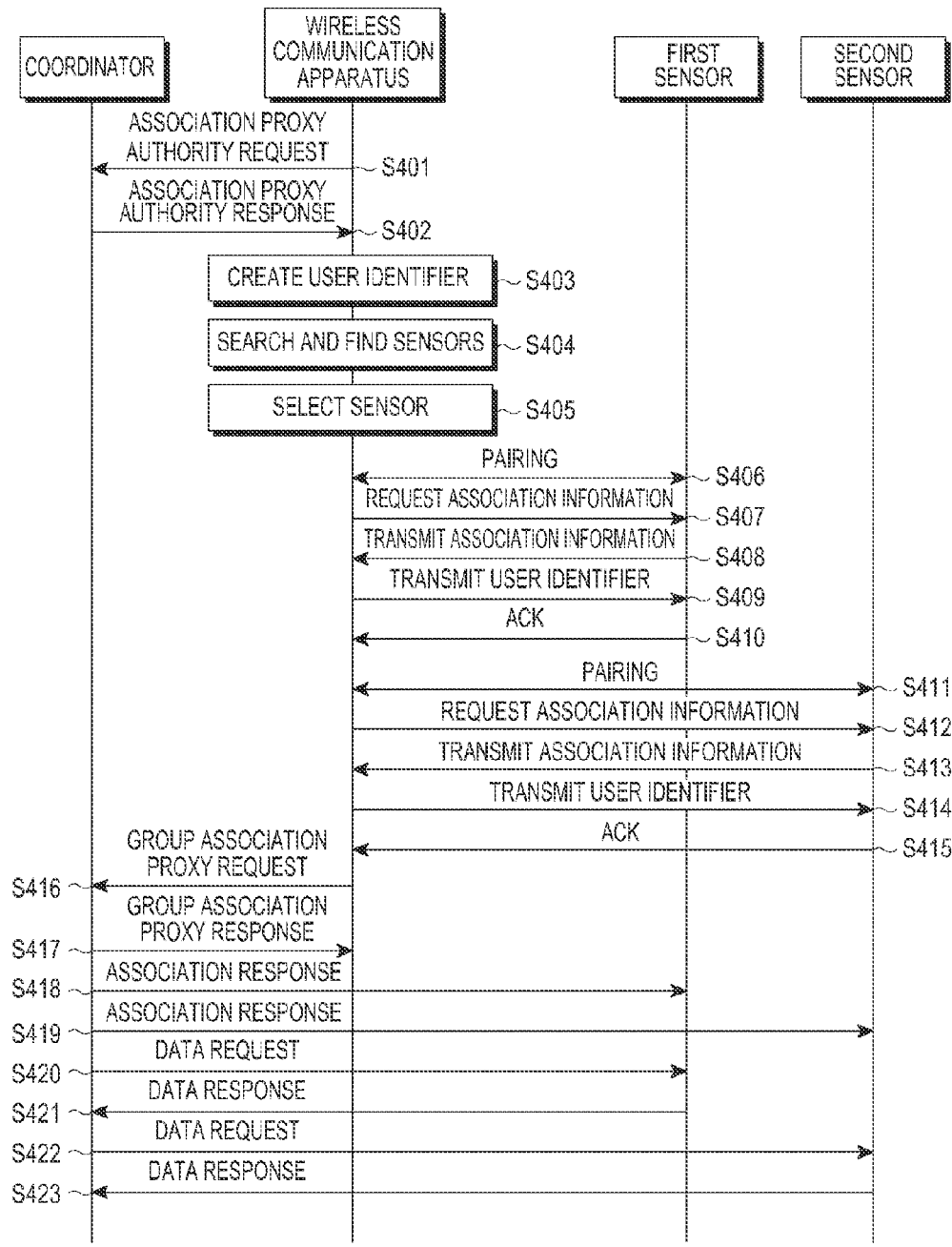
FIG. 4 is a timing diagram related to a control method of a communication system according to another embodiment of the present invention.

FIG. 4 is a timing diagram related to a control method of a communication system according to another embodiment of the present invention. The control method of the communication system according to FIG. 4 is similar to the control method of the communication system according to FIG. 3a. However, the wireless communication apparatus may search for and find the sensor (S404), and select the sensor (S405) only once at the beginning of the control method of a communication system in FIG. 4, which is merely different from the control method of a communication system in FIG. 3a.

The control method of a communication system in FIG. 3a performs the step of searching for and finding the first and the second sensors twice (S304 and S311), while the control method of a communication system in FIG. 4 may perform the searching and finding of the sensor once to thereby find the first and second sensors (S404).

Configurations of other steps S401 to S403 and S406 to S423 of FIG. 4 may be implemented in the same manner as the configurations of FIG. 3a, so the detailed descriptions of other steps S401 to S403 and S406 to S423 will be omitted hereinafter.

Figure 5:
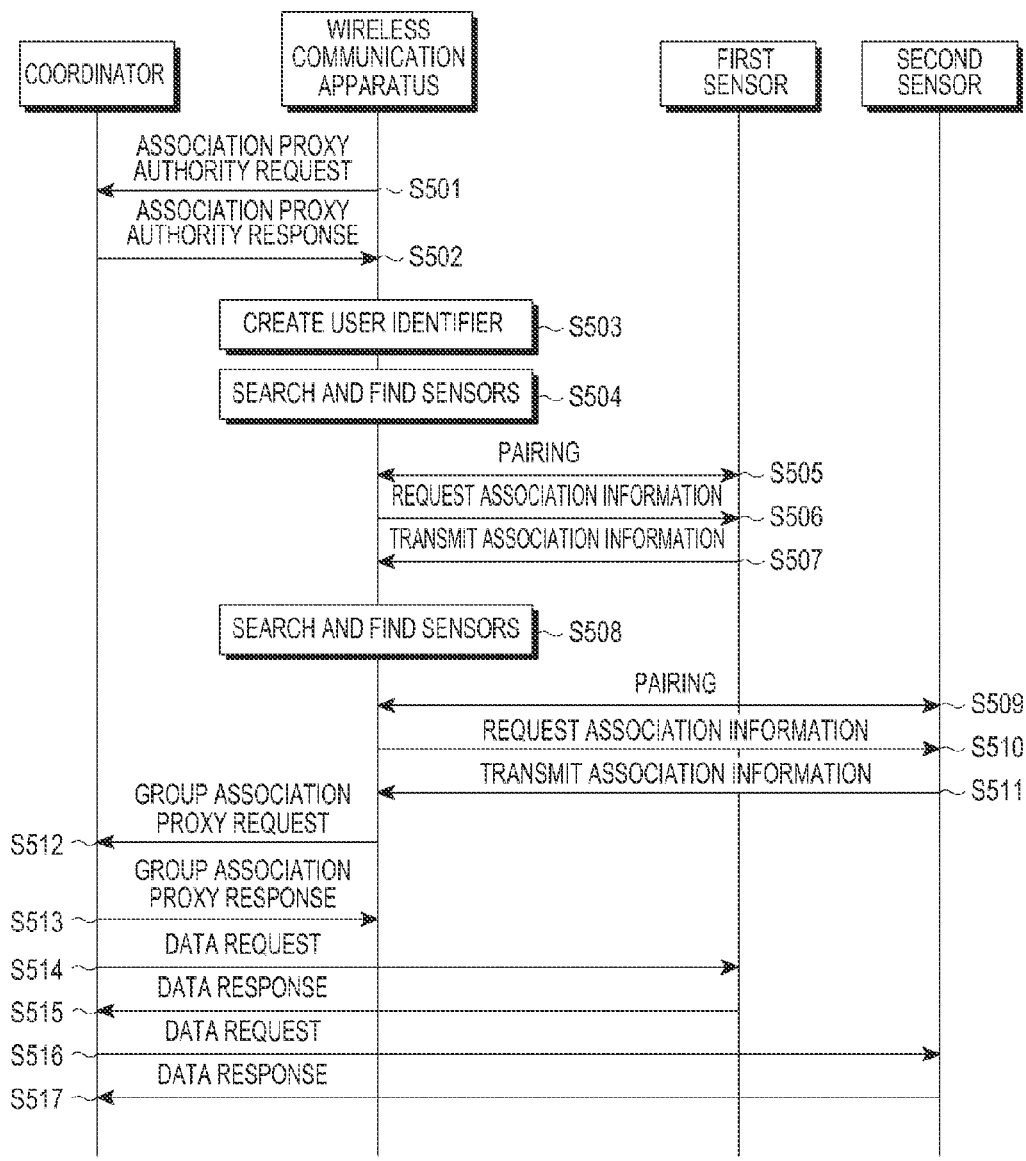
FIG. 5 is a timing diagram related to a control method of a communication system according to another embodiment of the present invention.

FIG. 5 shows a timing diagram related to a control method of a communication system according to another embodiment of the present invention. A first and a second sensors of the communication system in FIG. 5 do not include a storage means for storing the user identifier, in contrast to the first and the second sensors of the communication system in FIG. 3a.

Accordingly, in contrast to the wireless communication apparatus of the communication system in FIG. 3a, the wireless communication apparatus of the communication system in FIG. 5 forms the pairings with the first and the second sensors (S505 and S509), then requests the association information (S506 and S510), then receives the association information corresponding thereto (S507 and S511), and does not additionally provide the user identifier to the first and the second sensors.

A coordinator of the communication system in FIG. 5 may receive the user identifier in step S512 in which the group association proxy request is received, and construct a database by which the device ID list and the user identifier interwork, on the basis of the received user identifier. Meanwhile, configurations of other steps S501 to S511 and S513 to S517 of FIG. 5 may be implemented in the same manner as the configurations of FIG. 3a, so the detailed description of other steps S501 to S511 and S513 to S517 will be omitted hereinafter.

Figure 6A:
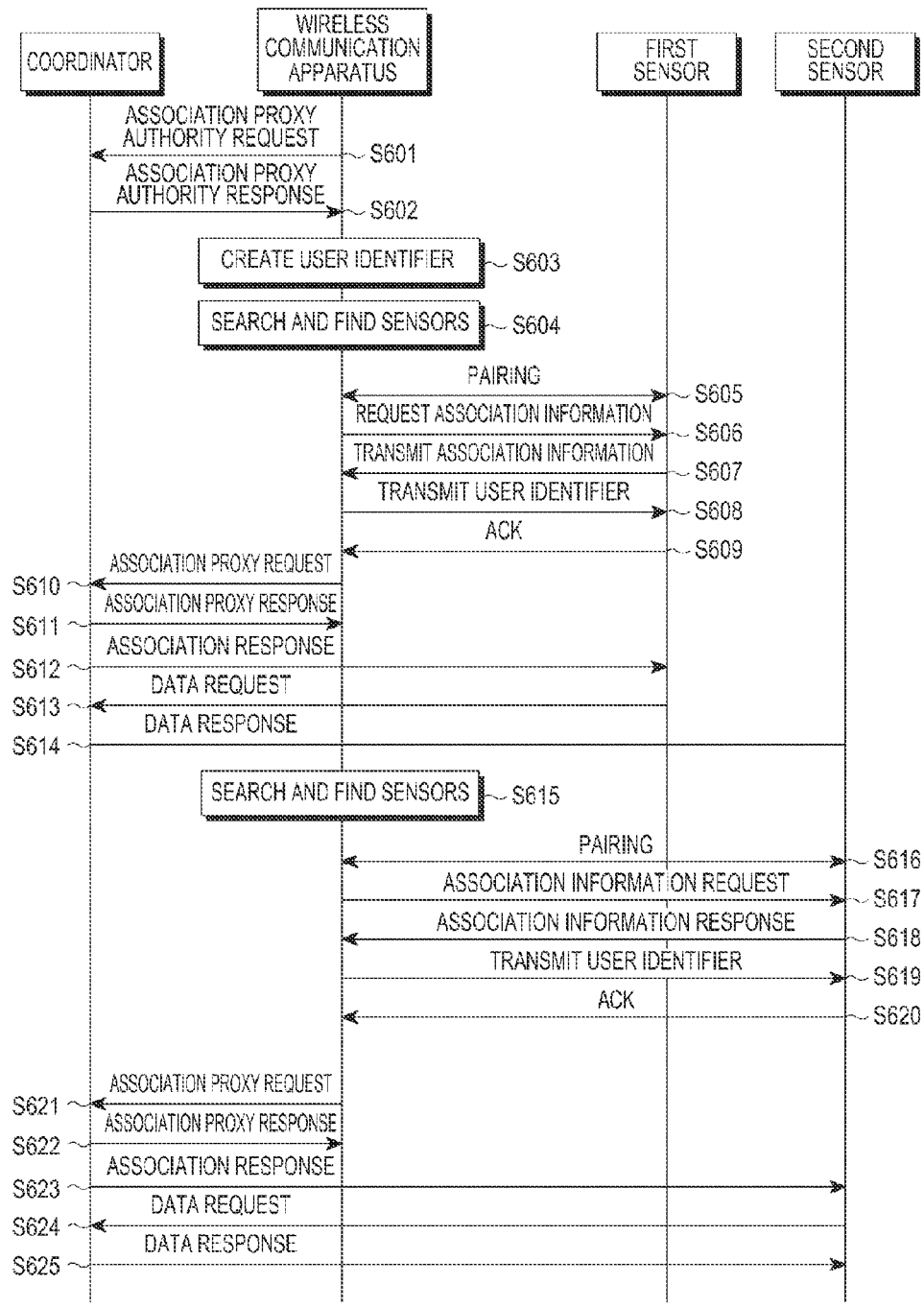
FIG. 6a is a timing diagram related to a control method of a communication system according to another embodiment of the present invention.

FIG. 6a shows a timing diagram related to a control method of a communication system according to another embodiment of the present invention. The control method of the communication system according to FIG. 6a is similar to the control method of the communication system according to FIG. 3a. Merely, the control method of the communication system in FIG. 6a does not provide the address pool when granting the proxy authority. Accordingly, the wireless communication apparatus does not provide the address when the wireless communication apparatus requests the first sensor for the association information. Further, just after the wireless communication apparatus completes the pairing with the first sensor (S605) and associating operation (S606 and S607), the association between the coordinator and the first sensor is formed (S610 and S611), and then transmission and reception of data between the coordinator and the first sensor is performed (S613 and S614). The transmission and reception of data may be performed after the pairings with the sensors are terminated. Afterwards, when the data reception of the coordinator from the first sensor is finished, the pairing between the second sensor and the wireless communication apparatus is formed (S616), and then associating operation (S617 and S618), forming association (S621 and S622), and transmission and reception of data (S624 and S625) are performed.

Meanwhile, the wireless communication apparatus according to FIG. 6a may request a single association proxy instead of the group association proxy in the steps S610 and S621 where the wireless communication apparatus requests the association proxy. Accordingly, the association proxy may include only single sensor information, for example, the first sensor information or the second sensor information, not the sensor information list. Further, the address to be used by the sensor may be included when transmitting the single association proxy response.

Figure 6B:
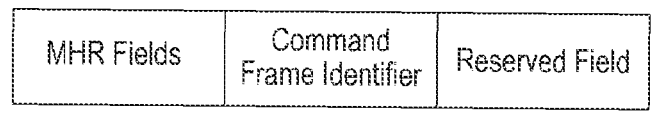
Figure 6C:
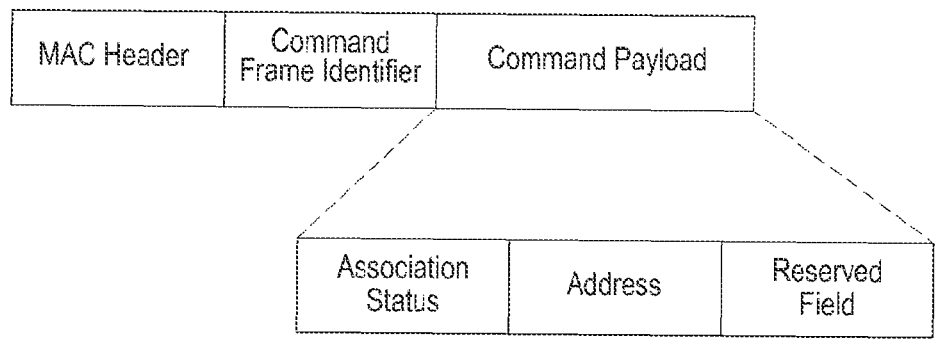

According to this, FIG. 6b may not include the address field in contrast to FIG. 3e, and FIG. 6c may additionally include the address field in contrast to FIG. 3 i.

Figure 7:
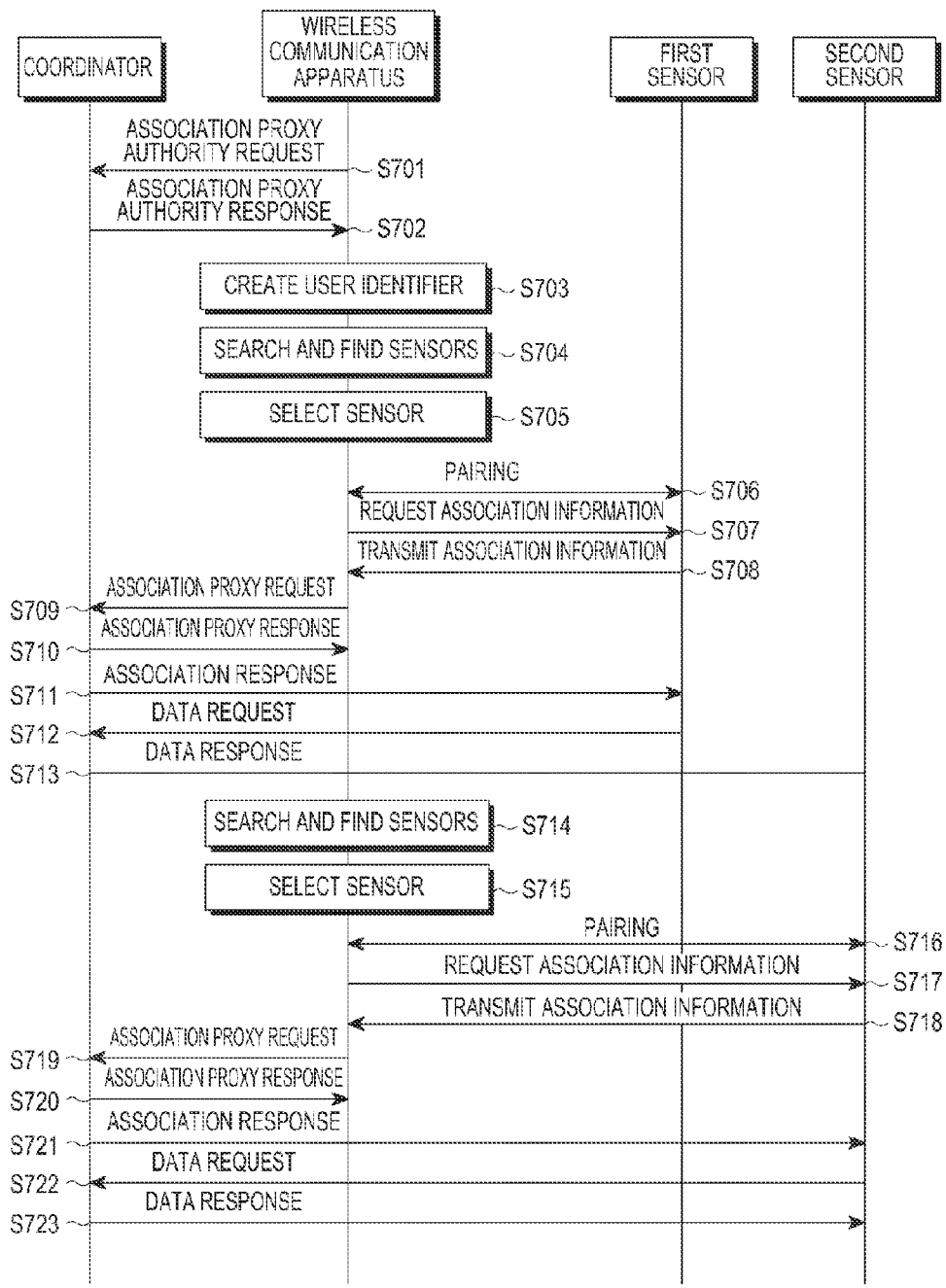
FIG. 7 is a timing diagram related to a control method of a communication system according to another embodiment of the present invention.

FIG. 7 shows a timing diagram related to a control method of a communication system according to another embodiment of the present invention. A first and a second sensors of the communication system on FIG. 7 do not include a storage means for storing the user identifier in contrast to the first and the second sensors of the communication system in FIG. 6.

Accordingly, in contrast to the wireless communication apparatus of the communication system in FIG. 6, the wireless communication apparatus of the communication system in FIG. 7 forms the pairings with the first and the second sensors (S706 and S716), then requests the association information (S707 and S717), then receives the association information corresponding thereto (S708 and S718), and does not additionally provide the user identifier to the first and the second sensors.

A coordinator of the communication system in FIG. 7 may receive the user identifier in the steps S709 and S719 in which the respective association proxy request is received, and construct the database by which the device ID list and the user identifier interwork, on the basis of the received user identifier. Meanwhile, configurations of other steps of FIG. 7 may be implemented in the same manner as the configurations of FIG. 3a, so the detailed description of other steps will be omitted hereinafter.

Meanwhile, in the control methods of communication system according to FIGS. 6 and 7, in contrast to the control methods of FIGS. 4 and 5, the coordinator may not transmit the address to be used by the sensor at the time when the wireless communication apparatus requests the association information, and may transmit the address at the time of the association response (S612, S622, S710 and S720).

Meanwhile, configurations of other steps except for the steps S602, S606, S612, S702, S707 and S711 in FIGS. 6 and 7 may be implemented in the same manner as the configurations of FIG. 3a, so the detailed description of other steps except for the steps S602, S606, S612, S702, S707 and S711 will be omitted hereinafter.

Figure 8:
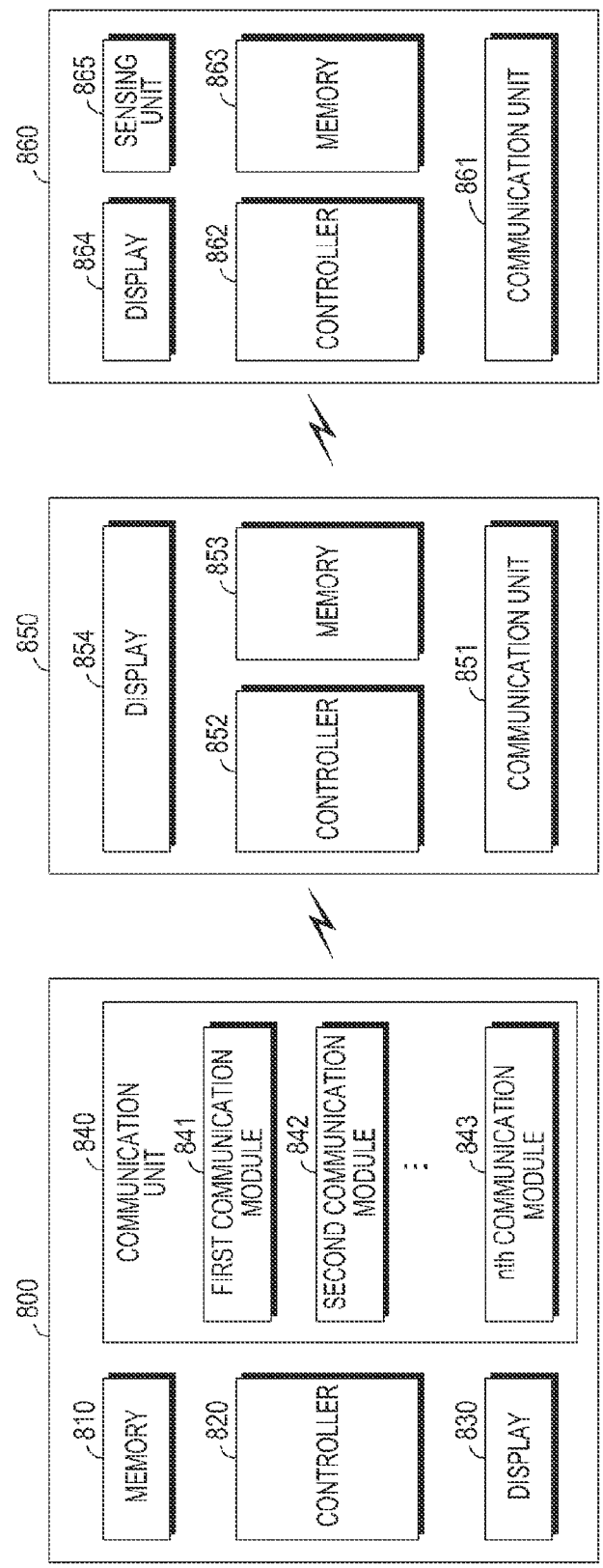
FIG. 8 is a block diagram of a communication system according to an embodiment of the present invention.

FIG. 8 is a block diagram of a communication system according to an embodiment of the present invention.

As shown in FIG. 8, a coordinator 800 may include a memory 810, a controller 820, a display 830, and a communication unit 840, and the communication unit 840 may include a first, a second and nth communication modules 841, 842 and 843. A wireless communication apparatus 850 may include a communication unit 851, a controller 852, a memory 853, and a display 854. A sensor 860 may include a communication unit 861, a controller 862, a memory 863, a display 864, and a sensing unit 865. Meanwhile, for the convenience of explanation, the elements included in the coordinator 800 will be prefixed with "the first", and the elements included in the wireless communication apparatus 850 will be prefixed with "the second". In addition, the elements included in the sensor 860 will be prefixed with "the third".

The first communication unit 840 may receive proxy authority request data for a proxy with respect to at least one sensor 860 and the coordinator 800 from the wireless communication apparatus 850. Meanwhile, each of the communication modules 841, 842 and 843 of the first communication unit 840 may perform wireless communication by different communication techniques, respectively, and in this regard, the detailed description was set forth above with reference to FIG. 1, so the more detailed description will be omitted hereinafter.

The first controller 820 may control the first coordinator unit 840 to transmit the proxy authority in response to the proxy authority request data.

The memory 810 may store the proxy authority request data, the user identifier information and sensor information that are additionally received, or data received from the sensor. The memory 810 may store a table by which each of the user identifier information is paired with at least one piece of sensor information. The memory 810 may store algorithms, programs or applications, which are required for the operation of the coordinator 800, and various parameters related thereto. The memory 810 may be implemented in the form of RAMs, ROMs or EEPROMs.

The display 830 may be a means for displaying information on data that is processed by the controller 820 in order to allow the administrator to recognize it, and it would be obvious to those skilled in the art that the display has no limitation as long as it is a means capable of outputting audio-visual information.

Meanwhile, the second communication unit 851 may receive the proxy authority.

The second controller 852 may create a user identifier corresponding to the user and control the second communication unit 851 to search for at least one sensor that the user wears and to form the pairing with the at least one found sensor.

Meanwhile, the memory 853 may receive and store the grant of the association proxy authority message from the coordinator, and store a plurality of created user identifiers, an identifier of the wireless communication apparatus 850, association information request data that is created to be transmitted to the sensor 860 later. Further, the memory 853 may store algorithms, programs or applications required for the operation, and various parameters related thereto. In addition, the memory 853 may store a table by which each piece of user identifier information is paired with at least one piece of sensor information, being synchronized with the coordinator.

The memory 853 may be implemented in the form of RAMs, ROMs or EEPROMs.

The display 854 may be a means for displaying information on data that is processed by the controller 852 in order to allow the administrator to recognize it, and it would be obvious to those skilled in the art that the display has no limitation as long as it is a means capable of outputting audio-visual information.

The third communication unit 861 may receive the association information request for the association between the coordinator 800 and the sensor 860 from the wireless communication apparatus 850. The third controller 862 may control the third communication unit 861 to transmit the association information to the wireless communication apparatus 850 in response to the association information request. The sensing unit 865 may detect bio-signals output from the body of the user, or process the same to be suitable for data transmission.

Here, the second controller 852 may control the second communication unit 851 to make a request to the coordinator 800 for the association proxy for the association between the at least one found sensor 860 and the coordinator 800.

The second communication unit 851 may receive the association proxy in response to the request, and the first controller 820 may control the first communication unit 840 to form the association with the at least one found sensor for the data request.

The third controller 862 may control the third communication unit 861 to transmit data in response to the data request.

Meanwhile, the sensor 860 may further include the storage unit 863 for storing at least one user identifier as set forth above, and the second controller 852 may control the second communication unit 851 to transmit the user identifier to the at least one found sensor 860.

Meanwhile, the second controller 852 may create the user identifier on the basis of the external input for the user identifier, or create the user identifier on the basis of RF signals received from RF generating means located around the user.

Meanwhile, the second controller 852 may control the second communication unit 851 to form pairings on the basis of the near-field communication (NFC) technique.

Here, when the at least one found sensor uses the identical communication technique, the second controller 852 may control the second communication unit 851 to form each pairing of the at least one found sensor sequentially.

The association information may include at least one of the identifier of the sensor 860 and information of the sensor 860. The information of the sensor 860 may be at least one of the serial number, the type, and the battery type of the sensor 860. If the coordinator 800 includes the database with the information on the sensor 860, the association information may include the identifier of the sensor 860 only. If the coordinator does not include the database with the information on the sensor 860, the first controller 820 may construct the database of the identifier list of the sensor 860 on the basis of the user identifier.

Meanwhile, the second controller 852 may control the second communication unit 851 to form the pairings with respect to some of the found sensors 860. Here, the second controller 852 may select some sensors on the basis of the external input signal. In addition, the second controller 852 may select some sensors on the basis of the intensity of signal received from the sensor 860. For example, the second controller 852 may control the second communication unit 851 to form the pairing with respect to the sensors whose signal intensity is equal to or more than the pre-set value.

The association proxy may include at least one of the identifier of the wireless communication apparatus 850, the user identifier, and the information of each found sensor 860.

The second controller 852 may control the second communication unit 852 to transmit the identifier of the wireless communication apparatus 850 together with the proxy authority request data.

In addition, the second controller 852 may control the second communication unit 851 to additionally transmit the information of the coordinator 800 together with the association information. In this case, the information of the coordinator 800 may be information on the address where the data received from the at least one found sensor 860 is stored.

Figure 9A:
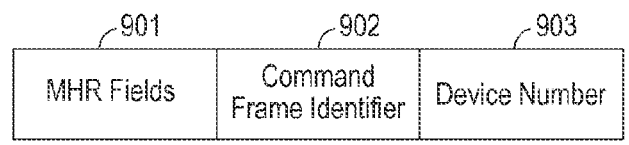
FIGS. 9a and 9b are conceptual diagrams of data fields of association proxy authority command frames, in relation to another embodiment of the present invention.

FIG. 9*a* is a conceptual diagram of data fields of an association proxy authority command frame, in relation to another embodiment of the present invention. As shown in FIG. 9*a*, the association proxy authority command frame may include an MHR field 901, a command frame identifier 902, and device number 903. Here, the MHR field 901 is a MAC header. The command frame identifier 902 refers to the type of the MAC command, and here, it may be the authority request command. The device number field 903 denotes the number of devices, for example, the number of sensors that the wireless communication apparatus is to use. The coordinator receives the number of devices and determines the number of necessary device addresses using the number of devices.

Figure 9B:
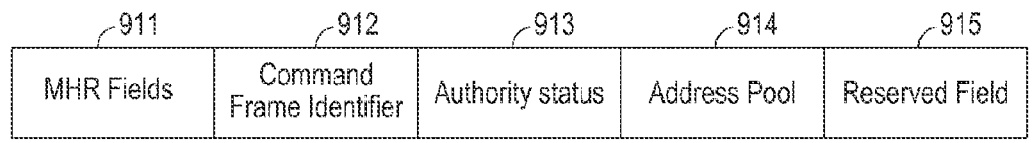

FIG. 9*b* is a conceptual diagram of data fields of an association proxy authority response command frame according to an embodiment of the present invention. As shown in FIG. 9*b*, the association proxy authority response command frame may include an MHR field 911, a command frame identifier 912, an authority status 913, an address pool 914, and reserved fields 915.

Here, the MHR field 911 is a MAC header. The command frame identifier 912 refers to the type of the MAC command, and here, it may be the authority response command. The authority status 913 indicates the result of the authority response, and the address pool 914 is the address information of each device that the wireless communication apparatus transmits to the device. It is characterized that the length of the address of each device is 16 bits or 64 bits. The size of the address pool is determined by reflecting the length of address information of each sensor to the device number received in the association proxy authority command frame or a pre-set value. The reserved fields 915 are allotted for later use.

Figure 9C:
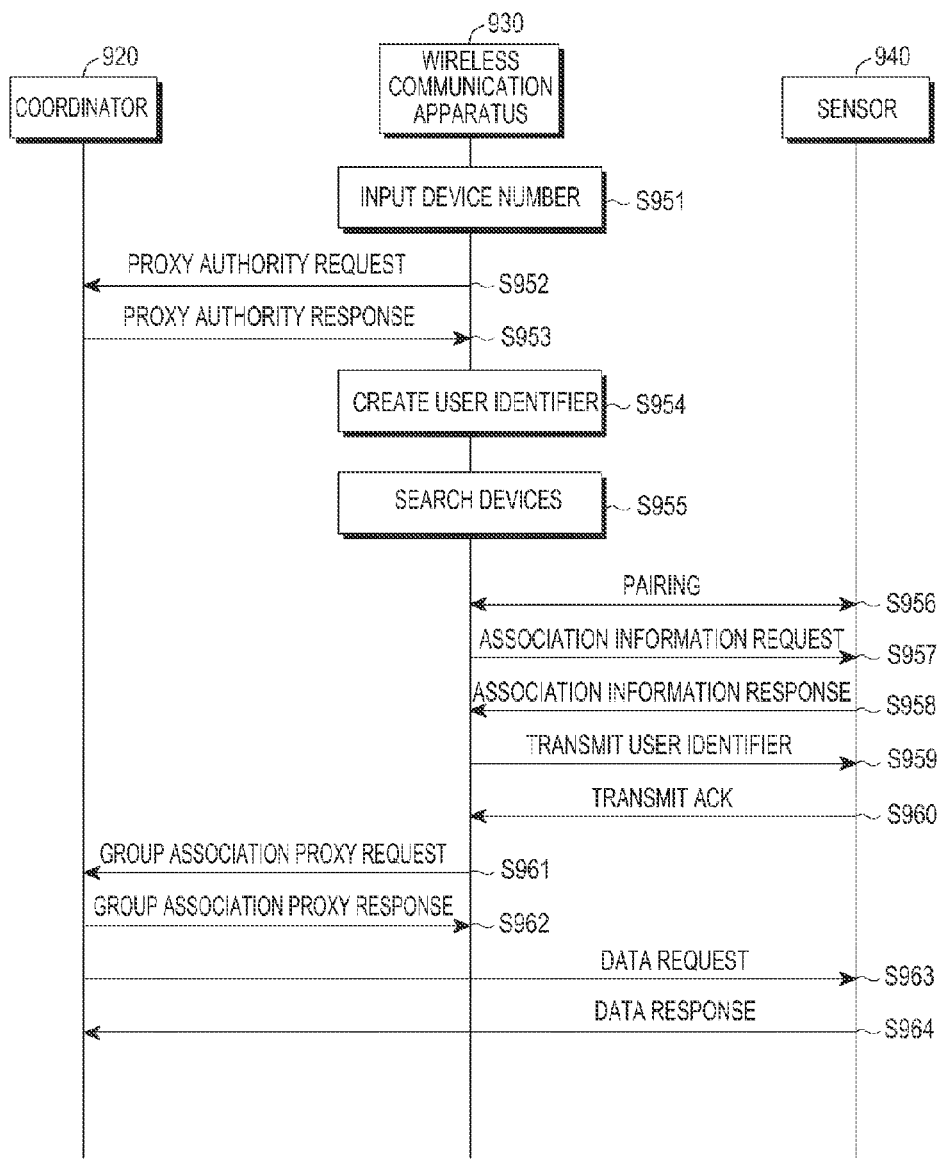
FIG. 9c is a timing diagram of a control method of a communication system according to an embodiment of the present invention.

FIG. 9*c* is a timing diagram of a control method of a communication system according to an embodiment of the present invention. The communication system of FIG. 9*c* includes a coordinator 920 and a wireless communication apparatus 930, and it is assumed that the wireless communication apparatus searches for and finds a single sensor 940 in the embodiment of FIG. 9*c*.

As shown in FIG. 9*c*, the user or the wireless communication apparatus 930 may input the device number (S951). Here, the device number is, for example, the number of sensors 940. The wireless communication apparatus 930 may request the proxy authority from the coordinator 920 (S952). Here, the proxy authority may be requesting the authority by which the wireless communication apparatus may act as a proxy for some or all of functions of the coordinator. For example, the authorized wireless communication apparatus may act as a proxy for the connecting operation between the coordinator and the sensor.

The coordinator 920 may grant the proxy authority to the wireless communication apparatus 930 in response to the proxy authority request (S953).

The wireless communication apparatus 930 may preferentially create a user identifier corresponding to the user who wears the sensor on the basis of the received proxy authority (S954). The user identifier may be used to provide information on the user wearing the each sensor 940 later.

Here, the wireless communication apparatus 930 may create the user identifier on the basis of an external input. Alternatively, the wireless communication apparatus may create the user identifier on the basis of RF signals received from a RFID tag or a RF signal generator around the user in relation to user information. Apart from that, the wireless communication apparatus 930 may create the user identifier in various ways, and it would be easily understood by those skilled in the art that there is no limitation in relation to the procedure of creating the user identifier.

The wireless communication apparatus 930 may search for and find the sensor 940 around the wireless communication apparatus 930 (S955). The wireless communication apparatus 930 may broadcast an inquiry packet in order to search for the sensor 940 around as set forth above, and check the received response packet or the like corresponding thereto to thereby find the sensor around the wireless communication apparatus. Preferably, the wireless communication apparatus 930 may search for the sensor 940 on the basis of the super near-field communication technique such as NFC.

The wireless communication apparatus 930 may form a pairing with respect to the found sensor 940 (S956). Here, the wireless communication apparatus 930 may form the pairings with respect to all of the found sensors 940, or some of the found sensors 940 on the basis of the external input signal for selecting sensors.

The wireless communication apparatus 930 may request the sensor 940 for association information for the association of the coordinator 920 and the sensor 940 (S957). Here, the association information may include information on a MAC header and the sensor.

Meanwhile, the sensors 940 may include communication modules like IEEE 802.15.4 Zigbee communication module. The sensor 940 may keep the communication module disabled, and when the association information request signal is received, the sensor 940 may convert the communication module to the enabled state. The communication module may wait until the data request is received from the coordinator 920.

The sensor 940 may transmit the association information in response to the received association information request (S958).

When the wireless communication apparatus 930 receives the association information from the sensor 940 (S958), it may transmit the created user identifier to the sensor 940 (S959). The sensor 940 may store the received user identifier in the storage medium that is provided in the sensor. The sensor 940 that has received the user identifier may transmit the acknowledge message to the wireless communication apparatus 930 (S960).

Meanwhile, if the sensor 940 is not provided with a special additional storage medium, the step of transmitting the user identifier by the wireless communication apparatus 930 may be omitted. After the user identifier is stored, the sensor 940 may transmit the user identifier information at the time when data is transmitted to the coordinator 920, so as to allow the coordinator 920 to easily analyze which user wears the sensor 940.

The wireless communication apparatus 930 may request the coordinator 920 for the association proxy for the association between the coordinator 920 and the sensor 940 (S961).

Here, the association proxy may include the identifier of the wireless communication apparatus 930, the user identifier, the information of the sensor 940, or the like.

The coordinator 920 may transmit a response to the association proxy to the wireless communication apparatus 930 (S962). The coordinator 920 may receive the association proxy request, and transmit the response thereto, so that the association between the coordinator 920 and the sensor 940 can be achieved.

The coordinator 920 may request predetermined data from the sensor 940 (S963). Here, the data may be bio-signals collected by the sensor 940 from the body of the user or data processed in a pre-set manner.

The sensor 940 may transmit the data to the coordinator 920 in response to the data request of the coordinator 920 (S964). Alternatively, even though the coordinator 920 does not request the transmission of data, the sensor 940 may periodically transmit information that is monitored to the coordinator 920.

Figure 10A:
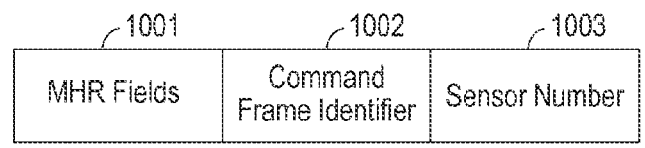
FIGS. 10a and 10b are conceptual diagrams of data fields of association proxy authority command frames, in relation to another embodiment of the present invention.

FIG. 10a is a conceptual diagram of data fields of an association proxy authority command frame, in relation to another embodiment of the present invention. As shown in FIG. 10a, the association proxy authority command frame may include an MHR field 1001, a command frame identifier 1002, and sensor number 1003. Here, the MHR field 1001 is a MAC header. The command frame identifier 1002 refers to the type of the MAC command, and it may be the authority request command, here. The sensor number field 1003 may be determined by inputting the user ID from the user or by using QR codes, bar codes, NFC, or the like as shown in FIG. 10c (S1051). In this way, the wireless communication apparatus may determine the device number necessary for the patient, and transmit the device number to the coordinator. This is used for notifying the necessary number of device addresses.

Figure 10B:
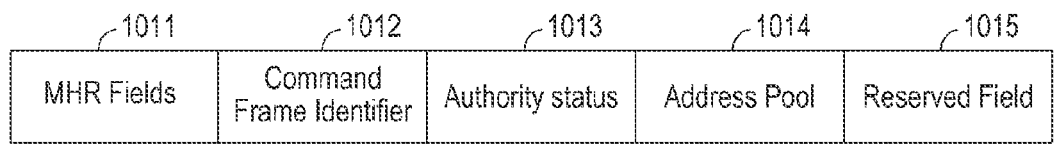
Figure 10C:
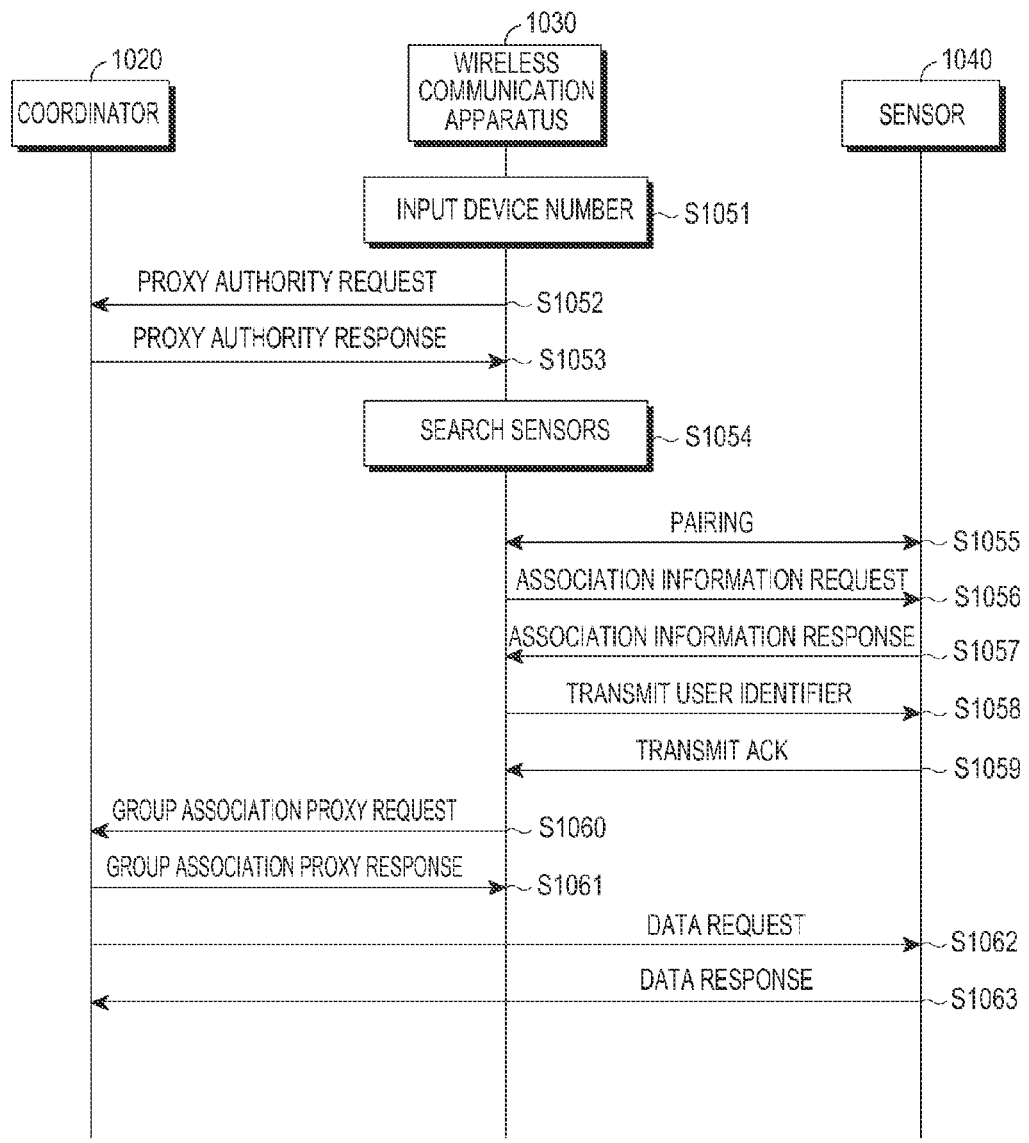
FIG. 10c is a timing diagram of a control method of a communication system according to an embodiment of the present invention.

FIG. 10b is a conceptual diagram of data fields of an association proxy authority response command frame according to an embodiment of the present invention. As shown in FIG. 10b, the association proxy authority response command frame may include an MHR field 1011, a command frame identifier 1012, an authority status 1013, an address pool 1014, and reserved fields 1015, and the detailed description thereof will be the same as in FIG. 9b.

FIG. 10c is a timing diagram of a control method of a communication system according to another embodiment of the present invention. In FIG. 10c, the user or the wireless communication apparatus 1030 may input the number of sensors 1040 in step S1051. Further, the wireless communication apparatus 1030 searches for the sensor 1040 in step S1054. The coordinator 1020 may perform the communication with the wireless communication apparatus 1030 and the sensor 1040. Meanwhile, the detailed description about steps S1052, S1053, and S1055 to S1063 in FIG. 10c will be the same as in FIG. 9c.

Figure 11A:
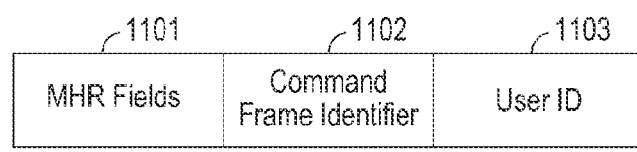
FIGS. 11a and 11b are conceptual diagrams of data fields of association proxy authority command frames, in relation to another embodiment of the present invention.

FIG. 11a is a conceptual diagram of data fields of an association proxy authority command frame, in relation to another embodiment of the present invention. As shown in FIG. 11a, the association proxy authority command frame may include an MHR field 1101, a command frame identifier 1102, and a user ID 1103. Here, the MHR field 1101 is a MAC header. The command frame identifier 1102 refers to the type of the MAC command, and here, it may be the authority request command. The user ID field 1103 denotes IDs of the patients who will use at least one device or IDs of persons who are to be measured using a plurality of devices. The user ID field may be determined by the user input or by collecting patient information around using QR codes, bar codes, NFC, or the like as shown in FIG. 11c.

Figure 11B:
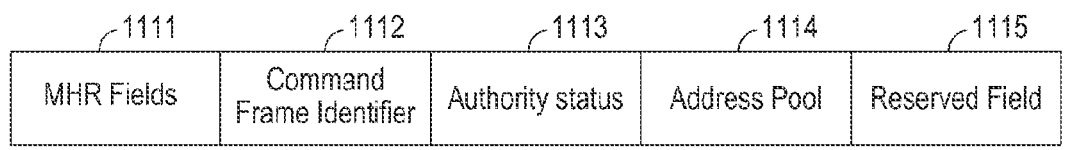

FIG. 11b is a conceptual diagram of data fields of an association proxy authority response command frame according to an embodiment of the present invention. As shown in FIG. 11b, the association proxy authority response command frame may include an MHR field 1111, a command frame identifier 1112, an authority status 1113, an address pool 1114, and reserved fields 1115.

Here, the MHR field 1111 is a MAC header. The command frame identifier 1112 refers to the type of the MAC command, and here, it may be the authority response command. The authority status 1113 indicates the result of the authority response, and the address pool 1114 is address information of each device that the wireless communication apparatus transmits to the device. It is characterized that the length of the address information is 16 bits or 64 bits. The size of the address pool 1114 is based on the user ID received in the association proxy authority command frame. The coordinator searches for the user ID stored in the coordinator, which corresponds to the received user ID, and determines device information necessary for the corresponding user ID. The size of the address pool may be recognized on the basis of the determined device number and the address information. The reserved fields 1115 are allotted for later use.

Figure 11C:
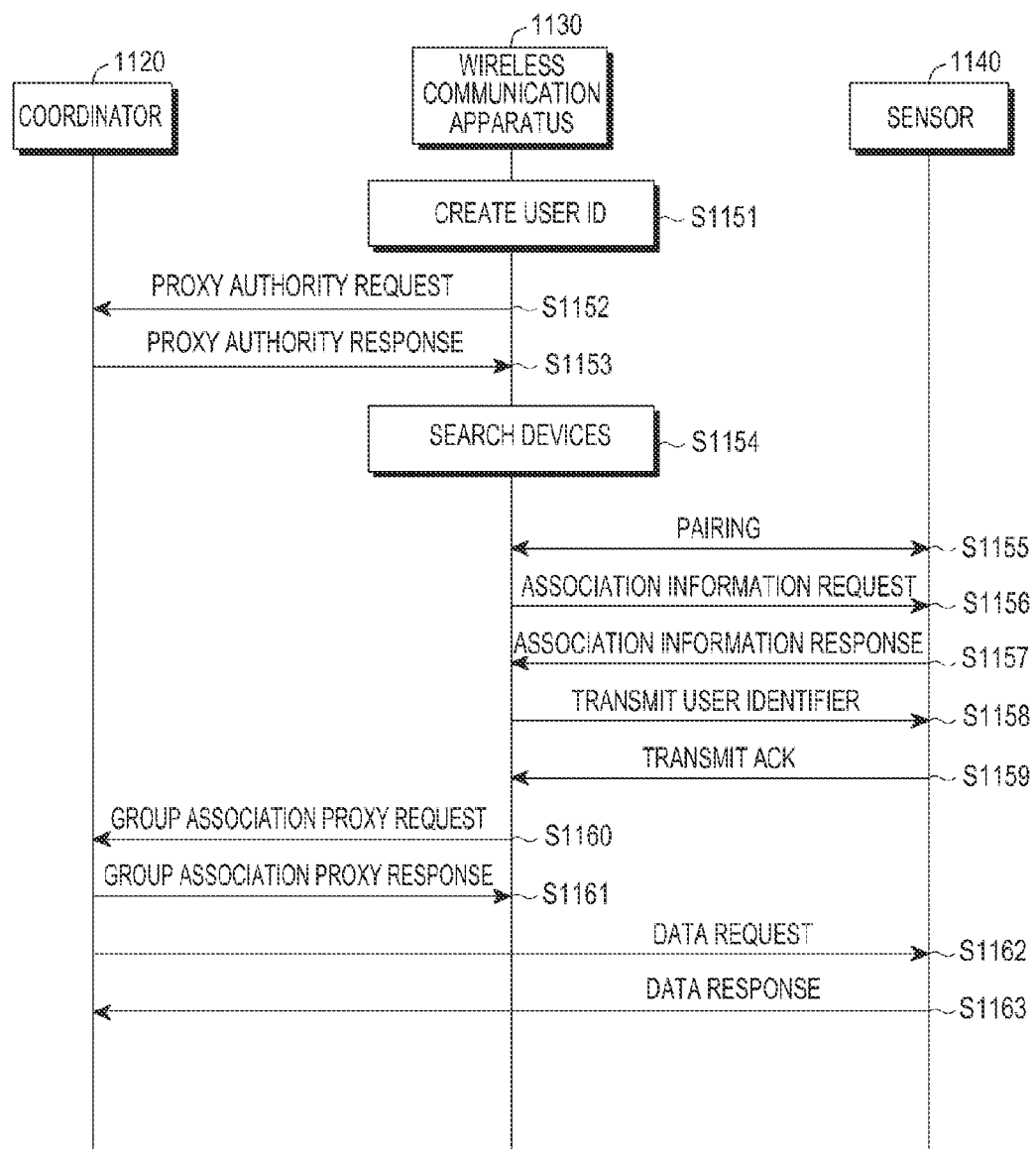
FIG. 11c is a timing diagram of a control method of a communication system according to an embodiment of the present invention.

Meanwhile, FIG. 11c is a timing diagram of a control method of a communication system according to another embodiment of the present invention. In FIG. 11c, the user or the wireless communication apparatus 1130 may create a user ID in step S1151. Furthermore, the wireless communication apparatus 1130 searches for the sensor 1140 in step S1154. The coordinator 1120 may perform the communication with the wireless communication apparatus 1130 and the sensor 1140. Meanwhile, the description about steps S1152, S1153, and S1155 to S1163 in FIG. 11c will be the same as in FIG. 9c.

While the present invention has been shown and described with reference to certain embodiments thereof, it will be understood by those skilled in the art that various changes in form and details may be made therein without departing from the spirit and scope of the present invention as defined by the appended claims. Therefore, various modified implementations can be made without departing from the substance of the present invention claimed in the appended claims, and the modified implementations should not be construed separately from the technical idea or prospect of the present invention.

The invention claimed is:

1. A control method of a communication system including at least one sensor that a user wears, a wireless communication apparatus and a coordinator, the method comprising:
   transmitting, by the wireless communication apparatus, a proxy authority request for proxy with respect to the at least one sensor and the coordinator to the coordinator, and receiving a proxy authority from the coordinator;
   creating, by the wireless communication apparatus, a user identifier corresponding to the user who wears the at least one sensor;
   searching, by the wireless communication apparatus, for the at least one sensor that the user wears, and forming a pairing with the at least one searched sensor;
   transmitting, by the wireless communication apparatus, a request to the at least one searched sensor for association information for the association with the coordinator and the sensor, and receiving the association information, the request for association information comprising information on the coordinator and the association information comprising an identifier of the at least one searched sensor; and
   transmitting, by the wireless communication apparatus, a request to the coordinator for an association proxy for the association between the at least one searched sensor and the coordinator, and receiving the association proxy comprising the identifier of the at least one searched sensor in response to the request for direct communication between the coordinator and the at least one searched sensor.

2. The method as claimed in claim 1, further comprising, after the receiving the association information, transmitting, by the wireless communication apparatus, the user identifier to the at least one searched sensor.

3. The method as claimed in claim 1, wherein, in the creating the user identifier, the user identifier is created on the basis of an external input for the user identifier.

4. The method as claimed in claim 1, wherein, in creating the user identifier, the user identifier is created on the basis of a RF signal received from an RF signal generating means located around the user.

5. The method as claimed in claim 1, wherein, in the forming of the pairing, the pairing is formed on the basis of the near-field communication (NFC) technique.

6. The method as claimed in claim 1, wherein, in the forming of the pairing, when the type of communication technique that the at least one searched sensor uses is identical, the pairing with respect to each of the at least one searched sensor is formed sequentially.

7. The method as claimed in claim 1, wherein the association information further comprises information on the sensor.

8. The method as claimed in claim 7, wherein the information on the sensor is at least one of a serial number, a form, and a battery type of the sensor.

9. The method as claimed in claim 7, wherein, if the coordinator includes the database with the information on the sensor, the association proxy comprises the identifier of the sensor.

10. The method as claimed in claim 7, wherein, if the coordinator does not include the database with the information on the sensor, an identifier list database of the sensor is constructed on the basis of the user identifier by the coordinator.

11. The method as claimed in claim 1, wherein, in the forming of the pairing with the at least one searched sensor, the pairing is formed with respect to only some of the searched sensors.

12. The method as claimed in claim 11, wherein the some of the searched sensors are selected on the basis of an external input signal.

13. The method as claimed in claim 11, wherein the some of the searched sensors are selected on the basis of the intensity of signal received from the searched sensors.

14. The method as claimed in claim 1, wherein the association proxy comprises at least one of an identifier of the wireless communication apparatus, the user identifier, and information of each of the searched sensors.

15. The method as claimed in claim 1, wherein, in the transmitting a request for the proxy authority, the wireless communication apparatus transmits an identifier of the wireless communication apparatus together.

16. The method as claimed in claim 1, wherein the information on the coordinator is information on the address where the data received from the at least one searched sensor is stored.

17. A communication system including at least one sensor that a user wears, a wireless communication apparatus and a coordinator,
the wireless communication apparatus comprising:
a communication unit configured to:
transmit a proxy authority request for proxy with respect to the at least one sensor and the coordinator to the coordinator, and
receive a proxy authority from the coordinator; and
a controller configured to:
create a user identifier corresponding to the user who wears the at least one sensor,
control the communication unit to search for the at least one sensor that the user wears to form a pairing with the at least one searched sensor,
transmit a request to the at least one searched sensor for association information for the association with the coordinator and the at least one searched sensor, and receive the association information, and
transmit a request to the coordinator for an association proxy for the association between the at least one searched sensor and the coordinator, and receive the association proxy comprising an identifier of the at least one searched sensor in response to the request for direct communication between the coordinator and the at least one searched sensor,
wherein the request for association information comprises information on the coordinator and the association information comprises the identifier of the at least one searched sensor.

18. The communication system as claimed in claim 17, wherein each of the at least one searched sensor further comprises a storage unit that stores the user identifier, and the controller controls the communication unit to transmit the user identifier to the at least one searched sensor.

19. The communication system as claimed in claim 17, wherein the controller creates the user identifier on the basis of an external input for the user identifier.

20. The communication system as claimed in claim 17, wherein the controller creates the user identifier on the basis of a RF signal received from an RF signal generating means located around the user.

21. The communication system as claimed in claim 17, wherein the controller controls the communication unit to form the pairing on the basis of the near-field communication (NFC) technique.

22. The communication system as claimed in claim 17, wherein, when the type of communication technique that the at least one searched sensor uses is identical, the controller controls the communication unit to sequentially form the pairing with respect to each of the at least one searched sensor.

23. The communication system as claimed in claim 17, wherein the association information further comprises information on the at least one searched sensor.

24. The communication system as claimed in claim 23, wherein the information on the at least one searched sensor is at least one of a serial number, a type, and a battery type of the at least one searched sensor.

25. The communication system as claimed in claim 23, wherein if the coordinator includes the database with the information on the at least one searched sensor, the association proxy comprises the identifier of the at least one searched sensor.

26. The communication system as claimed in claim 23, wherein if the coordinator does not include the database about the information of the at least one searched sensor, an identifier list database of the sensor is constructed on the basis of the user identifier by the coordinator.

27. The communication system as claimed in claim 17, wherein the controller controls the communication unit to form the pairing with respect to only some of the searched sensors.

28. The communication system as claimed in claim 27, wherein the controller selects the some of the searched sensors on the basis of an external input signal.

29. The communication system as claimed in claim 27, wherein the controller selects the some of the searched sensors on the basis of an intensity of signal received from the searched sensors.

30. The communication system as claimed in claim 17, wherein the association proxy comprises at least one of an identifier of the wireless communication apparatus, the user identifier, and information on each of the searched sensors.

31. The communication system as claimed in claim 17, wherein the controller controls the communication unit to transmit an identifier of the wireless communication apparatus together with the proxy authority request data.

32. The communication system as claimed in claim 17, wherein the information on the coordinator is information on the address where the data received from the at least one searched sensor is stored.

33. The communication system as claimed in claim 17, wherein the at least one sensor converts the third communication unit from a disabled state to an enabled state on the basis of the association information received from the wireless communication apparatus.

* * * * *